(12) United States Patent
Hirl (10) Patent No.: US 7,604,743 B2
(45) Date of Patent: *Oct. 20, 2009

(54) PROCESS FOR PRODUCING ETHANOL AND FOR ENERGY RECOVERY

(75) Inventor: Patrick Joseph Hirl, Minnetonka, MN (US)

(73) Assignee: Stanley Consultants, Inc., Muscatine, IA (US)

( * ) Notice: Subject to any disclaimer, the term of this patent is extended or adjusted under 35 U.S.C. 154(b) by 119 days.

This patent is subject to a terminal disclaimer.

(21) Appl. No.: 11/561,996

(22) Filed: Nov. 21, 2006

(65) Prior Publication Data

US 2007/0141691 A1 Jun. 21, 2007

Related U.S. Application Data

(60) Provisional application No. 60/751,792, filed on Dec. 19, 2005.

(51) Int. Cl.
*C02F 3/00* (2006.01)
*C12P 1/00* (2006.01)
*C12P 7/00* (2006.01)
*C12P 7/02* (2006.01)
*C12P 7/06* (2006.01)

(52) U.S. Cl. .................. 210/603; 210/606; 435/41; 435/132; 435/155; 435/161

(58) Field of Classification Search ........................ None
See application file for complete search history.

(56) References Cited

U.S. PATENT DOCUMENTS 6,299,774 B1 * 10/2001 Ainsworth et al. .......... 210/603

OTHER PUBLICATIONS

U. Tegtmeier "Process Design for Energy Saving Ethanol Production" Biotechnology Letters vol. 7 No. 2 129-134 (1985).*
Superiorpeat.com "Peat Moss" http://www.superiorpeat.com/products.htm, copyright 2003.*
Answers.com "Biogas" http://www.answers.com/topic/biogas accessed Jul. 24, 2009.*

* cited by examiner

*Primary Examiner*—L Blaine Lankford
*Assistant Examiner*—Thane Underdahl
(74) *Attorney, Agent, or Firm*—James P. Hanrath; Adam K. Sacharoff (57) ABSTRACT

The present invention is directed to a process for the production of ethanol and energy. The process includes the steps of fermenting a corn mash in an aqueous medium to produce a beer. Next, the beer is distilled to produce ethanol and a whole stillage. The whole stillage is anaerobically digested to produce a biogas and a residue. The biogas is combusted to produce electricity and steam. The electricity and steam are used during the fermentation and distillation process. The residue may further be separated into a liquid fertilizer and top soil residue.

15 Claims, 9 Drawing Sheets

5,000 Head Dairy and Ethanol Plant Anaerobic Digester System with Energy, Bedding, and Fertilizer Recovery

FIGURE 6

Dry Milling Process for Ethanol Production With Self-Generation of Energy

PROCESS FOR PRODUCING ETHANOL AND FOR ENERGY RECOVERY

CROSS REFERENCE TO RELATED APPLICATION

This application claims priority to U.S. Provisional Application 60/751,792 filed Dec. 19, 2005.

FIELD OF THE INVENTION

This invention relates to the production of ethanol and the conversion of ethanol production co-products (i.e., whole stillage, wet distillers' grain with solubles, and distillers dried grain with solubles) to energy.

BACKGROUND

Figure 1:
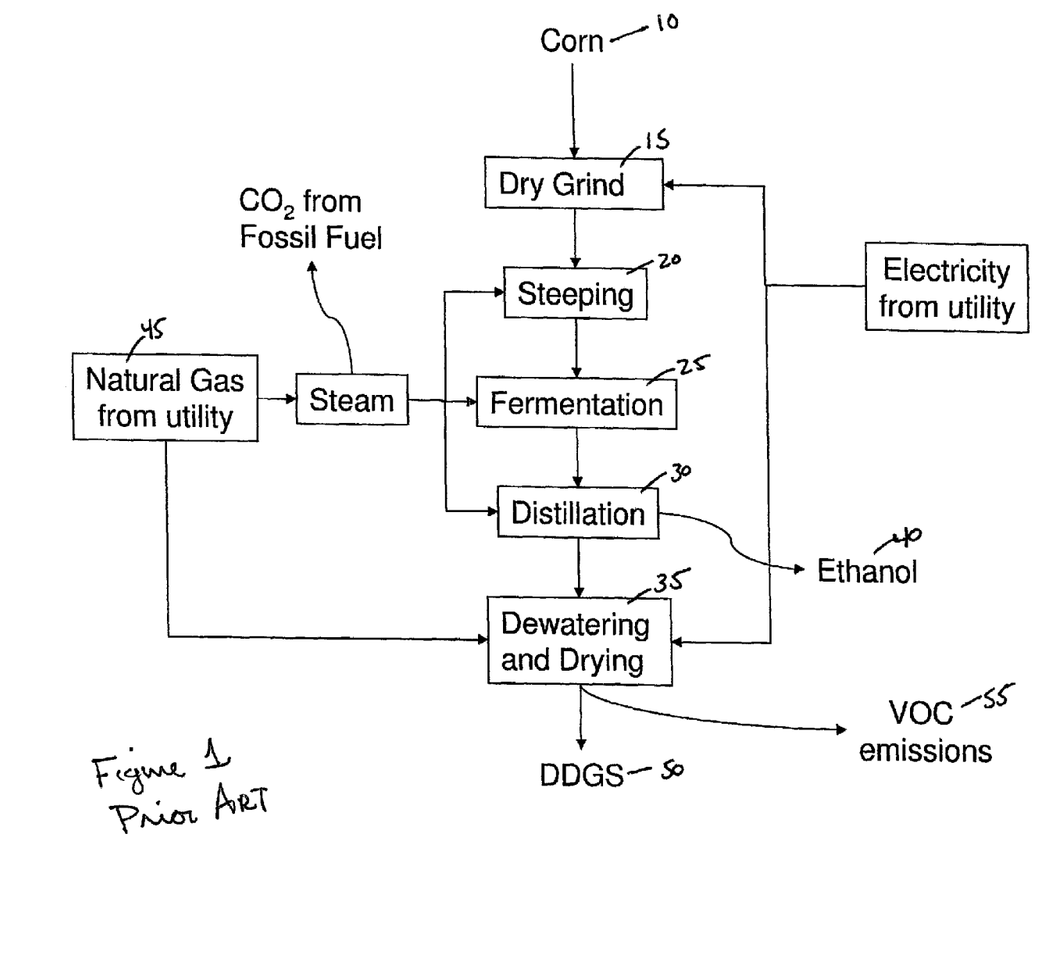
FIG. 1 illustrates a current ethanol production process known in the prior art.

The dry mill production of ethanol is well known in the Prior Art. In FIG. 1, there is shown one exemplary illustration of such a process in accordance to the prior art. First, corn 10 is mechanically grinded 15. The ground corn is mixed with water and enzymes in a steeping process 20 which creates a "mash". The mash is heated with yeast to promote fermentation 25 of the starches from the corn into ethanol. The fermented mash is distilled 30 and the ethanol is extracted 40. The now spent mash is dewatered and dried 35 to create distillers dried grains and solubes (DDGS) 50. The DDGS 50 is then sold or consumed by animals as feed stock.

The production of ethanol involves significant use of natural gas 45 (35,000-40,000 BTU/gallon of ethanol produced) and approximately a third of the natural gas consumed in the current ethanol process is used in the last step, to dry the mash to create a sellable product, DDGS. Moreover, the drying of the spent mash from the ethanol process to create the DDGS disadvantageously produces the emission of volatile organic compounds (VOC) 55.

While ethanol has become part of the United States' strategy to develop alternative fuels to eliminate reliance on oil and natural gas, there is significant controversy over whether or not it takes more energy, currently non-renewable energy, to produce a gallon of ethanol than the energy value of that gallon of ethanol. The most recent evaluation from the US Department of Agricultural concludes that ethanol has a positive net energy value (i.e., ethanol energy content—energy required for ethanol production); a significant increase in the net energy value for ethanol would accelerate its acceptance as an alternative fuel and its share of the liquid fuels market.

In one prior art reference, U.S. Pat. No. 6,355,456 discloses a process of using wet grain residue from ethanol production to feed livestock. The manure collected from livestock is used for the production of methane. The '456 patent produces wet distiller's grains and solubles, (hereinafter "WDGS") as a co-product of ethanol production. The WDGS is mixed with grain to produce cattle feed, which is fed to cattle in special barns with slatted floors in order to grow cattle and produce manure. The manure is placed into an anaerobic digester, where the manure is microbially converted to methane. The '456 patent further mechanically separates solids and liquids in the sludge from the manure, dries the solids, and sells the digested liquid and dry solids. The '456 further uses heat produced from the biogas combustion for dry milling the grain.

While the '456 patent has some advantages, it also has some disadvantages. For example, the livestock actually remove much of the energy and ammonia that are present in the WDGS, which could be recovered and used. The WDGS is used to feed and grow the cattle, rather than try to convert the WDGS to energy. The present invention improves upon the teachings of the '456 patent and provides for even greater advantages over the '456 patent, discussed in detail below.

SUMMARY OF THE INVENTION

In accordance with the present invention there is provided a new system and process for ethanol production that further involves anaerobic digestion of the whole stillage to convert it to biogas. The biogas generated is then used in place of natural gas in the ethanol production as well as for the production of electricity.

The anaerobic digestion (biological conversion of organic compounds to biogas or methane) of the whole stillage can generate more methane than the natural gas used in production of the ethanol. The excess methane can produce approximately 75% of the electricity required for ethanol production. The present invention has the potential for increasing the net energy value for ethanol by 9.6 times, significantly reducing the reliance of the ethanol industry on natural gas, and significantly reducing the financial exposure of the ethanol industry to two commodities with volatile pricing, natural gas and distiller's dried grains and solubles (DDGS). The invention further allows for the production of ammonia fertilizer from the whole stillage. Whole stillage contains approximately 20% protein, which is high in nitrogen. The anaerobic digestion process releases the nitrogen into the water as ammonia. The ammonia in the water can be recovered and used for fertilizer.

In one embodiment of the present invention, a process of producing ethanol is provided. The process includes grounding corn to produce a dry grind. The dry grind is mixed or soaked with water during a steeping process. Enzymes and yeast are added and then the mixture is fermented. After fermentation a beer is created which is distilled in order to extract ethanol.

It should be known that the actual processes of steeping, fermentation and distillation are well known in the industry and may include other additives or steps not disclosed herein, but would be included for proper processing of the corn to ethanol.

The ethanol is extracted from the beer leaving whole stillage. The whole stillage, anaerobic digester sludge, and recycled water are mechanically mixed together to create the mixed liquor in a slurry tank. The mixed liquor is pumped from the slurry tank to an anaerobic digester. The anaerobic digester is a continuous flow biological reactor which is either plug flow or completely mixed. The mixed liquor is mixed in the digester either mechanically or by sparging with biogas. The anaerobic digester is heated using heat from the combustion of biogas. The biogas is collected from the headspace of the anaerobic digester and used for: fuel in an internal combustion engine to produce electricity and fuel for a boiler to produce steam. The electricity produced is used to power mechanical systems in the ethanol production facility and the anaerobic digester system. The steam produced in the boiler is used in the production of ethanol. Waste heat is collected from the coolant of the internal combustion engine and the exhaust gas of the internal combustion engine using a fresh water system. The fresh water system is used to heat the anaerobic digester. After being in the anaerobic digester the mixed liquor is pumped from the digester to a screw press for separation of the digested solids from the digested liquid. The digested solids are dewatered and then sold as a soil amendment. The digested liquid is pumped into an air stripping tower for removal of the ammonia. The water following ammonia removal is recycled back to the slurry tank. The off-gas from the ammonia stripping tower goes into an ammonia recovery scrubber where the ammonia is recovered at a high concentration in water. The concentrated ammonia solution is then sold as fertilizer.

The invention advantageously will reduce VOC emissions from ethanol facilities by eliminating the source of the VOC (i.e., drying the whole stillage) and will reduce greenhouse gas emissions by creating the energy necessary for ethanol production from a renewable source (i.e., corn). The methane generated from anaerobically digested whole stillage came from carbon dioxide in the atmosphere through the growth of the corn plant. The invention will eliminate the need for natural gas in the ethanol production process and will reduce the electrical requirement by 75%. The energy reduction is achieved because natural gas is produced internally in the process through anaerobic digestion and electricity is also produced internally to the process.

The present invention has many advantages and differences over the '456 patent including: the use of whole stillage from the ethanol production process rather than the WDGS used in the '456 patent; the '456 patent mixes WDGS with grain to produce cattle feed, the present invention does not produce cattle feed; the '456 patent feeds cattle in special barns with slatted floors in order to grow cattle and produce manure, the present invention does not need cattle or special barns and does not produce manure as an intermediate product; the '456 patent puts manure into an anaerobic digester and microbially converts the manure to methane, the present invention creates a mixture of whole stillage, recycled anaerobic sludge, and recycled water to create a mixed liquor to be anaerobically digested to methane; the '456 patent mechanically separates the solids in the sludge from the liquid, dries the solids, and sells the digested liquid and dry solids, the present invention mechanically separates the solids from the digested mixed liquor, sells the solids without drying, recovers the ammonia in a concentrated liquid using air stripping and air scrubbing, and recycles the recovered water; and the '456 uses the heat produced from biogas combustion for dry milling grain, the present invention uses the heat from combustion of the biogas to produce electricity for ethanol production, steam for ethanol production, and recovers waste heat from electricity production to heat the anaerobic digester.

In one embodiment of the present invention an integrated continuous process for the production of ethanol and energy is provided. The process includes fermenting a corn mash in an aqueous medium to produce a beer. The beer is distilled to produce ethanol and a whole stillage. The whole stillage is mixed with water and bacteria and then anaerobically digested which produces a biogas and a residue. The biogas is combusted to produce electricity and steam. The electricity and steam is utilized for the fermentation and distillation of the ethanol.

The process may also include dehydrating the distilled ethanol to produce an ethanol with a higher proof then the aforementioned distilled ethanol. During the dehydrating step water is recovered and utilized during the distillation step.

The process may also separate the residue into digested liquids and digested sludge. The digested sludge is dewatered to produce a soil amendment and a residual water that is recycled into the whole stillage. The digested liquid may also be stripped of water and scrubbed to produce an ammonia solution.

BRIEF DESCRIPTION OF THE DRAWINGS

A fuller understanding of the foregoing may be had by reference to the accompanying drawings, wherein.

DESCRIPTION OF THE INVENTION

Figure 2:
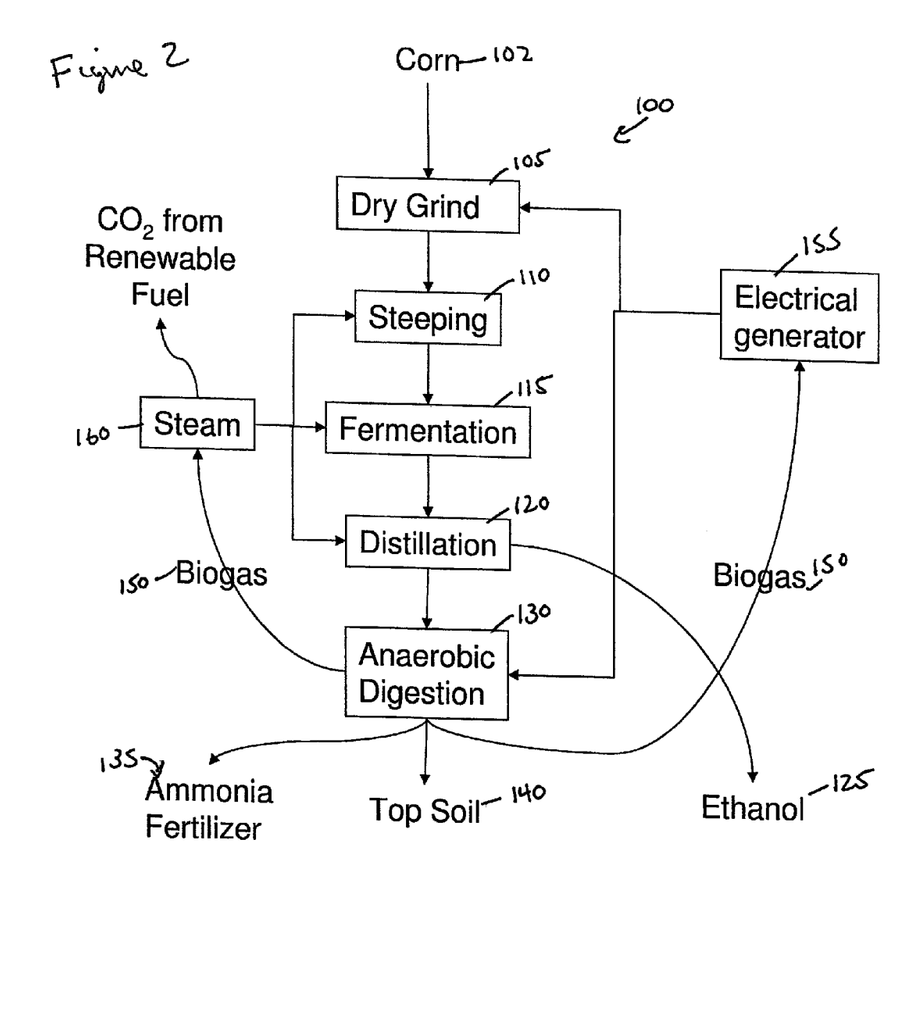
FIG. 2 illustrates a process of producing ethanol in accordance to an embodiment of the present invention.

Referring now to FIG. 2, there is shown and disclosed one embodiment of the present invention, which illustrates a process for the production of ethanol. In this first system 100, corn 102 is grounded 105 into a dry grind. The dry grind then undergoes a steepping process 110 where water and enzymes are added to produce a mash. The mash is then fermented with yeast, 115. The fermentation is then distilled 120, to extract ethanol 125. The spent mash or remainder goes into an anaerobic digester 130 which extracts ammonia fertilizer 135, top soil 140 and biogas 150. The biogas 150 is used to help power an electrical generator 155 and a steam generator 160 which is used in the system 100. The ammonia fertilizer 135 and top soil 140 may be sold and/or consumed on premise. In this first system, the DDGS or WDGS is not consumed by animals, rather the whole stillage is feed into the anaerobic digester 130 to extract the full amount of energy in the whole stillage.

The Development and use of Biomass for Energy Production.

Biomass can be converted to energy in several ways. Burning plant material, such as sawdust, is one method for conversion of biomass to energy. Collection and combustion of landfill gas is another. Many plant and animal tissues, including manure, can also be converted to methane by anaerobic microbial activity and the biogas produced (i.e., a mixture of methane and carbon dioxide) can be used as a fuel. It is through anaerobic microbial conversion to methane that many agricultural (e.g., manure) and agri-industry (e.g., distiller's grains and solubles) byproducts can be converted to fuel while leaving odorless organic matter and nutrients (i.e., ammonia nitrogen and phosphate) available for amendments to cropland.

In parallel with the energy sector promoting the development of renewable energy sources, the livestock industry is coming under increasing regulatory pressure to reduce the environmental impacts of concentrated animal feeding operations (CAFOs). The impacts of CAFOs on the environment focus on the management and disposal of manure. These impacts include airborne emissions of odorous organic compounds, hydrogen sulfide, and ammonia, release of raw liquid manure into water bodies (surface and groundwater), and the over application of phosphorus on fields due to manure application based on nitrogen content. The CAFO manure is a biomass energy source because of its methane generation potential through the use of anaerobic microorganisms. Anaerobic digestion of manure produces methane gas (i.e., natural gas) from this renewable energy source. In addition, anaerobic digestion of the manure will convert organic nitrogen to ammonia, cause precipitation of phosphorus as struvite, and eliminate volatile organic compounds that produce offensive odors. Thus, anaerobic digestion of manure reduces many of the CAFO impacts while producing renewable energy.

The following sections present an example of how distributed, renewable energy (on-farm anaerobic digestion of manure) can cost effectively meet many of the environmental challenges of CAFOs. In addition, a second example will be presented to show how a CAFO (e.g., large dairy) could be teamed with an energy intensive industry (e.g., ethanol production facility) to symbiotically use co-products and nutrients for the production of natural gas, electricity, ethanol, and milk.

Anaerobic Microbial Conversion

Anaerobic microbes are capable of generating energy from the oxidation of organic molecules without the use of oxygen. These organisms can reduce nitrate, sulfate, and carbon dioxide while oxidizing complex organic molecules. The products of anaerobic microbial metabolism are nitrogen gas, hydrogen sulfide, and, in the largest quantity, methane.

Anaerobic conversion of organic matter to methane occurs in a series of steps that are accomplished by different groups of organisms. The first step in the anaerobic process is hydrolysis. In this step complex organic polymers (i.e., starch, triglycerides, and proteins) are reduced to their monomers (i.e., glucose, fatty acids, and amino acids). The second step oxidizes these monomers to 3-5 carbon organic acids (i.e., propionic, butyric, and valeric acid). The third step converts these acids to acetic acid. The final step takes acetic acid, as well as carbon dioxide produced in earlier reactions, and converts them to methane. It should be noted that amino acids contain nitrogen. Through the anaerobic conversion of amino acids to methane, the nitrogen from the amino acids is released from the molecule as ammonia. Therefore, the anaerobic microbial activity also releases ammonia nitrogen from its organically bound state in the amino acid, making it more available for plant uptake.

The methane production from protein, starch, and fat can be approximated using microbial stoichiometry, a well known process. Based on the overall chemical reactions for methane production from these complex organic molecules, the methane generation capacities for each general group of molecules have been calculated (Table 1). The potential electricity that could be generated from the methane produced through anaerobic conversion was also calculated assuming a 25 percent efficient generator.

TABLE 1

METHANE PRODUCTION AND ELECTRICAL POWER GENERATION FROM COMPLEX ORGANIC MOLECULES AND MANURE

| Molecule | Methane Generation (ft3/lb) | Electricity Generated (kW-hr/lb) |
|---|---|---|
| Protein | 4.5 | 0.33 |
| Carbohydrate | 3.0 | 0.22 |
| Fat | 15.1 | 1.11 |
| Manure (volatile solids) | 6.1 | 0.45 |

Anaerobic Digester System

The conversion of organic molecules to methane by anaerobic microbes must occur in an environment void of oxygen. The rate of conversion will be proportional to the temperature of the environment and the number of microbes in the system.

Figure 3:
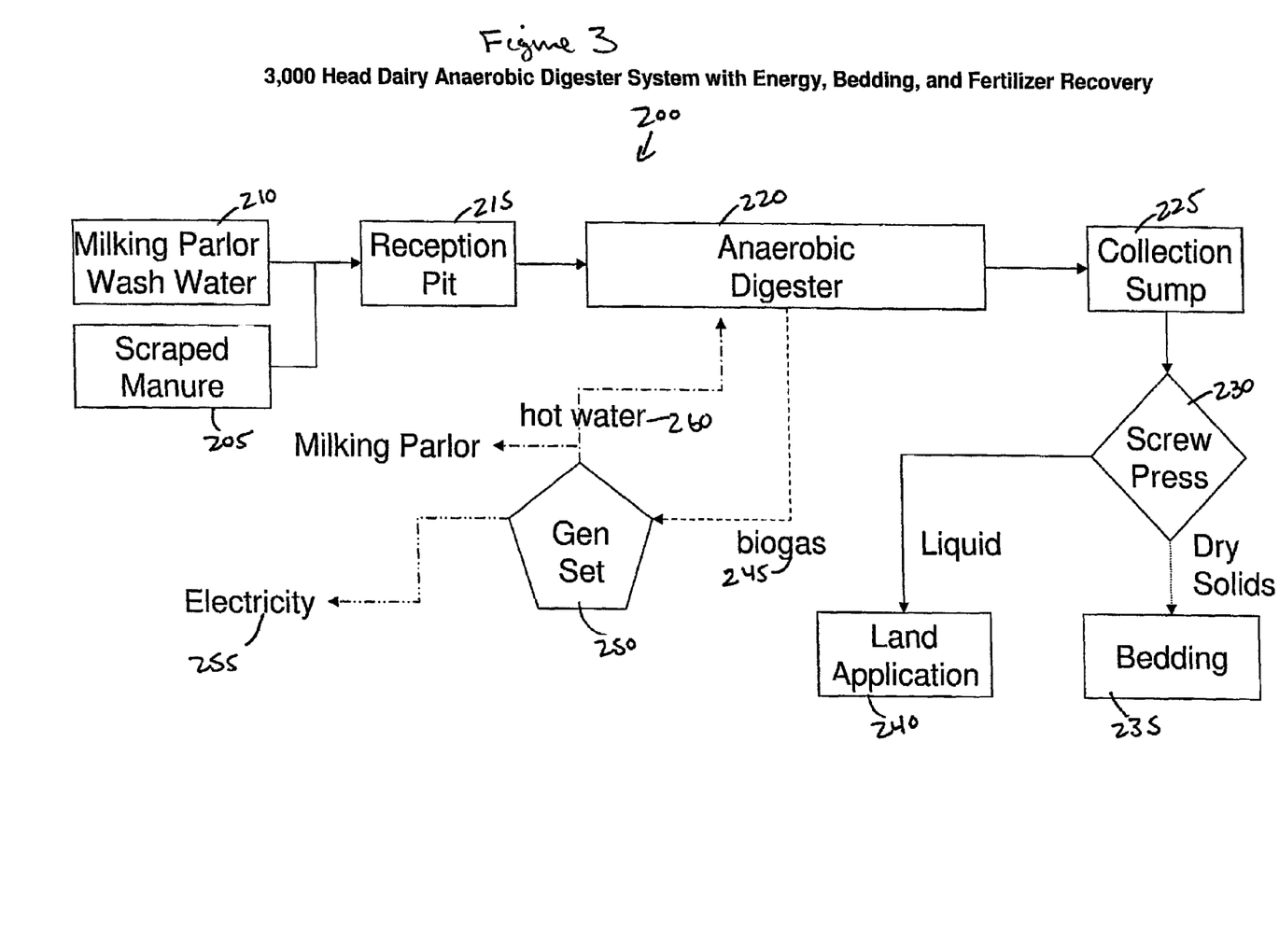
FIG. 3 illustrates a 3,000 head dairy anaerobic digester system in accordance to an embodiment of the present invention.

Referring now back to the figures, FIG. 3 presents a system 200 capable of converting dairy manure to methane gas. The system 200 would require maintaining the manure in an oxygen-free environment at approximately 100° F. for 15 to 20 days. Manure is scraped 205 from the stalls and the milking parlor wash water 210 are mixed together into a reception pit 215 creating a slurry. The slurry of approximately 8 percent solids is pumped into the concrete heated digester 220 for 15 to 20 days. The effluent from the digester 220 is then moved into a collection sump 225 where it is then mechanically dewatered by a screw press 230 or similar separator (such as a centrifuge) with the solids being used for animal bedding 235 and the liquid used for fertilizer 240. Biogas 245 from the digester 220 can be used by a generator 250 to produce electricity 255 and hot water 260, which can be used for the milking parlor wash water 210 and by the digester 220.

Figure 4:
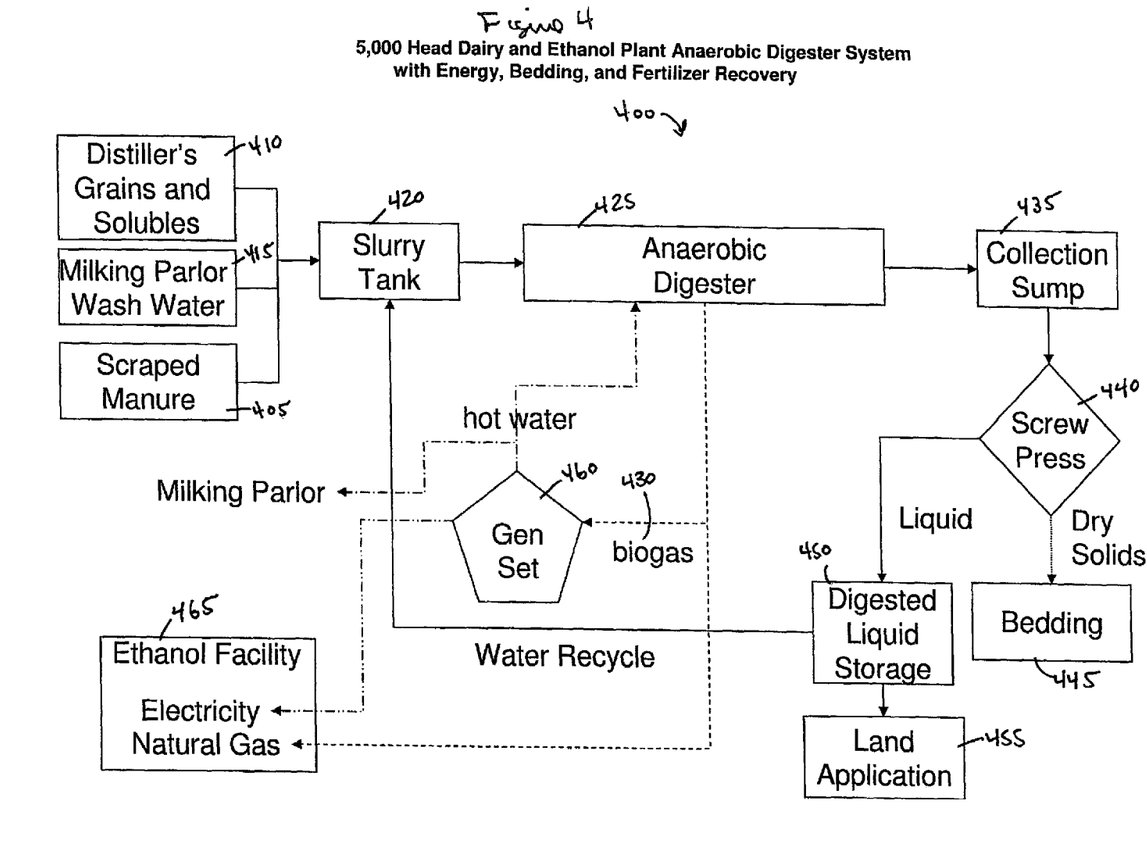
FIG. 4 illustrates a 5,000 head dairy and ethanol plant anaerobic digester system in accordance with an embodiment of the present invention.

A process flow diagram for the combined digestion of manure and distillers grains and solubles (DGS; ethanol plant byproduct) system 400 is presented in FIG. 4. The scraped manure 405, milking parlor wash water 415 and DGS 410 is added to a slurry tank 420 along with recycled water, if necessary. The recycled water would be used to ensure the influent to the anaerobic digester is between 10 percent and 15 percent solids content. The slurry is then pumped into a heated concrete plug flow anaerobic biological reactor or digester 425. The reactor is mixed, perpendicular to the axis of flow to prevent vertical stratification within the reactor while maintaining the plug flow. Biogas 430 is collected in the reactor headspace. After 15 to 20 days in the reactor the effluent slurry is moved to a collection sump 435 and is mechanically dewatered by a screw press 440. The solids are available for dairy bedding 445 or an organic soil amendment and the liquid can be recycled 450 into the slurry tank 420 and/or a liquid fertilizer 455. Thus the manure and DGS is converted to fuel (i.e., methane gas), fertilizer (i.e., ammonia in the separated liquid) and animal bedding or topsoil (i.e., the digested solids will have the properties of topsoil). The biogas 430 is used by a generator 460 to convert the same to electricity and hot water. The reactor is heated using a portion of methane gas generated either through a boiler or from the waste heat produced by an electrical generator. The electricity can be used to run the ethanol facility 465 which produces the DGS.

3,000-Head Dairy Example

As an example, consider a 3,000-head dairy (scrape manure collection) which produces approximately 60,000 gallons per day of liquid manure at 8 percent total solids (includes milking parlor wash water). Manure solids are approximately 86 percent volatile. Based on the information presented above, the methane generated from the manure is calculated at 219,600 ft$^3$ methane/day. This would equate to 220 mmBTU/day of natural gas or 16,100 kW-hr/day of electrical power (25 percent generation efficiency). Waste heat recovery from electrical power generation could also provide 60 mmBTU/day. A 1,400 lb. lactating dairy cow produces about 0.57 lb/day of nitrogen in its manure. This equates to 0.86 tons/day of nitrogen, which is equivalent to 1.1 tons/day of anhydrous ammonia fertilizer. The non-digested fiber in the anaerobic digester effluent will be approximately 15 lbs/day/cow. Half of the dewatered/air dried solids will be used for bedding. The remainder of the dried solids are sold.

An anaerobic digester with 650 kW of electrical generating capacity servicing the 3,000 head dairy would cost approximately $2,700,000. Electricity is sold to the local utility for $0.06/kW-hr. The state provides a $0.015/kW-hr renewable energy production incentive. Excess bedding is sold for $15/ton. Operation and maintenance of the digester and generators was estimated at $0.02/kW-hr. It is also assumed that the cost of the digester and generators are depreciated over a 10-year period and that the system owner can take full advantage of the depreciation loss. Based on these assumptions, a private investor could build, own, and operate an anaerobic digester based power generation system on a dairy farm and receive a return on investment (ROI) in excess of 12 percent.

Corn Grower—Ethanol Plant—Dairy Farm System

Figure 5:
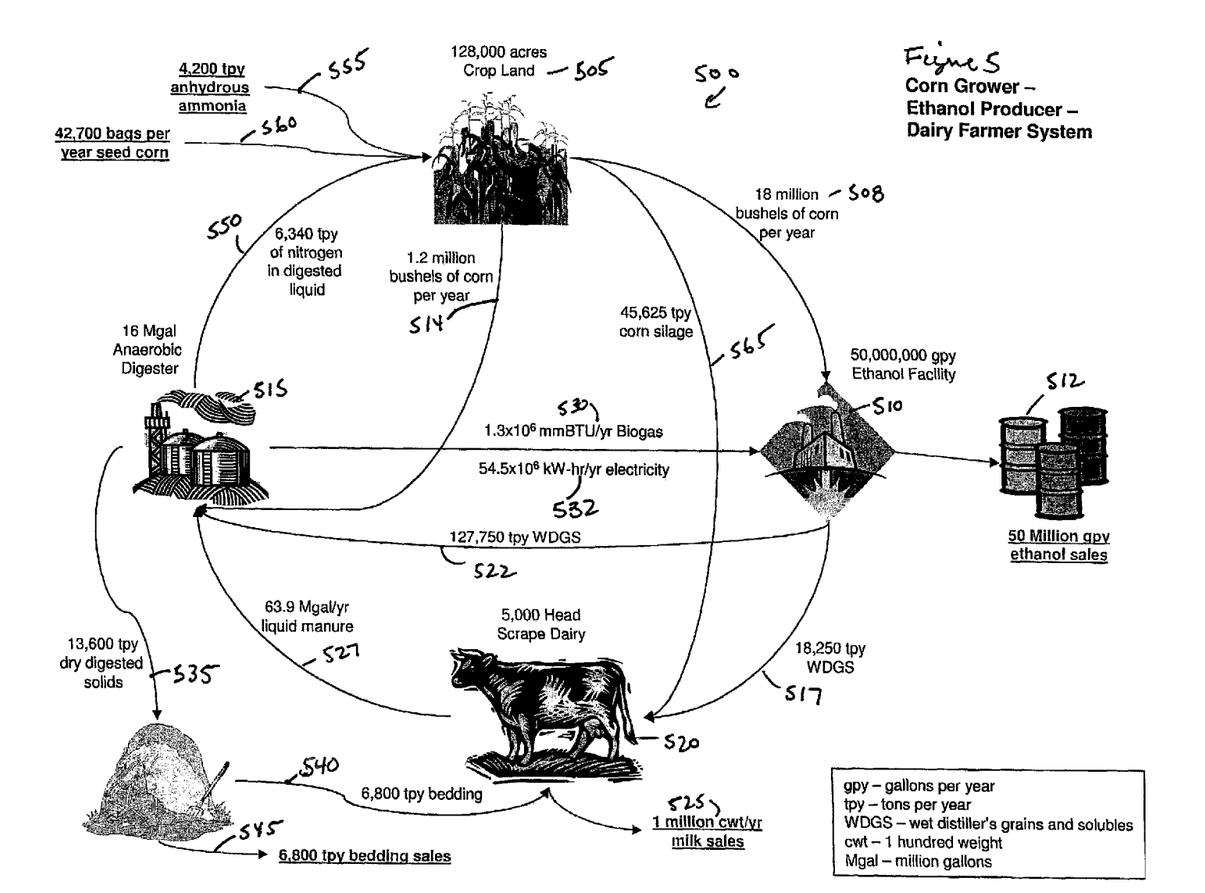
FIG. 5 illustrates a corn grower, ethanol producer and dairy farmer system in accordance with an embodiment of the present invention.

An approach to improving the energy efficiency of the biogas is to co-locate the anaerobic digester with a natural gas intensive process. In this example, a 50 million gallon per year ethanol production facility with an anaerobic digester is co-located with a 5,000-head dairy farm in a corn growing region. FIG. 5 presents the symbiotic relationship between the corn grower, ethanol producer, and dairy farmer.

As illustrated in FIG. 5, system 500 includes 128,000 acres of land 505 in the vicinity, 8-10 mile radius, of the ethanol facility 510. The land 505 is needed for growing 19.2 million bushels of corn. 18 million bushels 508 are used by an ethanol facility 510 to produce 50 million gallons of ethanol 512. 1.2 million bushels 514 are fed directly to the anaerobic digester 515 for additional energy production. 18,250 tons per year of wet distillers grains and solubles (WDGS) 517 are produced by the ethanol facility 510 and are consumed by the 5,000 dairy cows 520. 127,750 tons per year of WDGS 522 (produced by the ethanol facility 510) are sent directly to the anaerobic digester 515 for energy production. The 5,000 head of dairy cattle 520 produce 1 million hundred weight (cwt) of milk per year 525, which is bottled and sold, and produce 63.9 million gallons of liquid manure 527, which are sent annually to the anaerobic digester 515 for energy production.

The digester 515 produces 2.18 million mmBTU per year of biogas. 1.33 million mmBTU of the biogas 530 is used directly to produce steam for ethanol production. 0.85 million mmBTU are converted to electricity 532 for use in ethanol production. 13,600 tons of dried digested solids are produced each year by the anaerobic digester 535. 6,800 tons of the dried digested solids are used for bedding 540 at the diary farm, while 6,800 tons of the dried digested solids are sold 545 each year. The digested liquids contain 6,340 tons per year of ammonia nitrogen 550 that will be applied to the fields to support corn growth. An additional 4,200 tons per year of anhydrous ammonia 555 will be purchased in order to meet the growth requirements of the corn.

Therefore, with the addition of 4,200 tons per year of anhydrous ammonia and seed corn for 128,000 acres, this theoretical system could annually produce 50 million gallons of ethanol, 1 million cwt of milk, and 6,800 tons of bedding/compost.

This approach provides many environmental benefits to the ethanol facility and the dairy farmer. The ethanol facility does not need to dry the distillers grains and solubles thus eliminating ⅓ of their natural gas use, significantly reducing volatile organic compound (VOC) emissions, and eliminating the need for a thermal oxidation unit for managing VOC emissions. Odorous emissions from raw manure storage at the diary are significantly reduced because all manure is digested prior to storage eliminating noxious VOCs in the manure. The stored digested liquid will have significantly less biochemical oxygen demand thus reducing its potential effects on a receiving body of water should an accidental release occur. Finally, anaerobic digestion promotes precipitation of phosphorus such that the digested liquid will have significantly less phosphorus than raw manure. This will reduce the phosphorus load on fields when digested manure is applied at agronomic rates for nitrogen.

Assuming an existing dairy with neighboring corn farmers, the ethanol plant and digester could be constructed for approximately $80 million. Table 2 provides a theoretical annual balance sheet for the operation. It was assumed that ethanol is sold for $1.20/gal and milk is sold at $13.50/cwt.

TABLE 2

Annual Balance Sheet for Corn/Ethanol/Dairy System

| Category | Annual Debit/Credit ($ million) |
|---|---|
| Fertilizer | (1.47) |
| Seed Corn | (5.12) |
| Ethanol Facility O&M | (18.0) |
| Dairy Farm O&M | (8.65) |
| Corn Farm O&M | (8.53) |
| Ethanol Sales | 60.0 |
| Milk Sales | 13.5 |
| Bedding Sales | 0.10 |
| Ethanol Productive Incentive | 3.0 |
| Renewable Electricity Production Incentive | 0.82 |
| Annual Net Revenue | 35.65 |

Based on $35.65 million in annual revenue, corn growers would be paid an effective price of $2.10/bu for corn and the dairy farm would be paid an effective price of $14.45 cwt for milk. After these payments are made, the ethanol plant investors would receive approximately $11 million in profit. Assuming that the ethanol plant and digester are depreciated over 10 years, the ethanol plant investors would receive a minimum of 12 percent ROI. Thus, Anaerobic digestion can address many of the critical environmental issues facing CAFOs. Using a renewable energy approach, anaerobic digestion with electricity production on large dairy farms can be an attractive investment for a private investor interested in developing renewable energy. Further, bundling of agri-industry entities allowing for renewable energy production as well as raw material production and by-production utilization (i.e., corn production, ethanol production, and milk production) provides for the production of milk and ethanol with very little input of fossil fuels (fossil fuel input only through the production of the additional anhydrous ammonia purchased for corn production). This bundled system is not only an attractive investment, it also produces ethanol with a significantly reduced energy input and it provides control of volatile commodity prices (e.g., corn, natural gas, and DDGS) allowing the bundled organization to better manage its financial risk.

Figure 6:
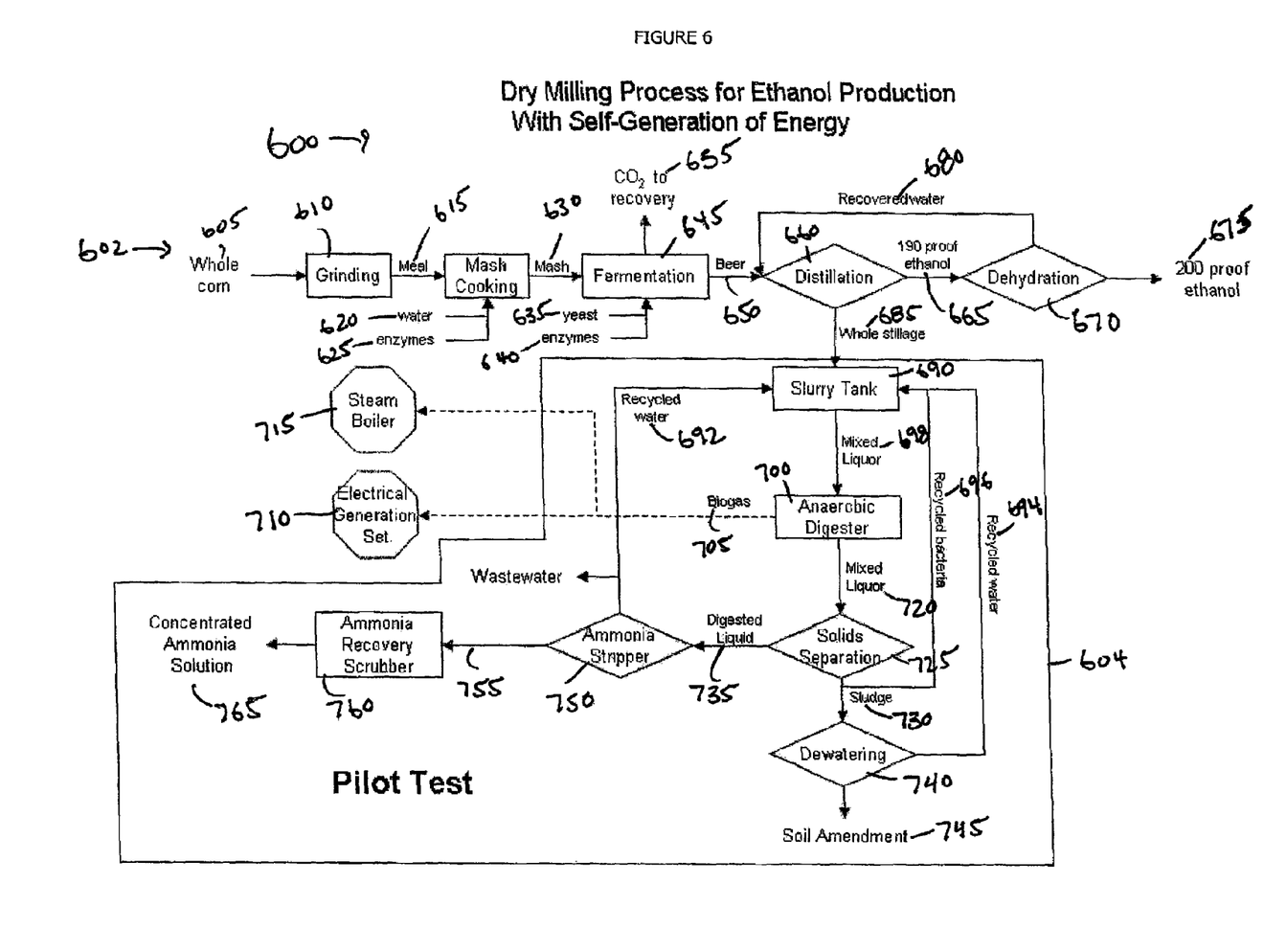
FIG. 6 illustrates a dry milling process for ethanol production with self generation of energy in accordance with an embodiment of the present invention.

Referring to FIG. 6, there is shown and disclosed one embodiment of the present invention, illustrating a system 600 that includes a process for the production of ethanol 602 and a process of self-generating energy 604. The process of producing ethanol 602 begins with whole corn 605 that is ground 610 to create a corn meal 615. The corn meal 615 is mixed with water 620 and enzymes 625 to create a mash 630. The mixing process is typically referred to as a steeping process. The mash 630 is mixed with yeast 635 and enzymes 640 and then fermented 645 to create a beer 650. During the fermentation process 645 carbon dioxide may be recovered 635. The beer 650 is then distilled 660 to create a 190 proof ethanol 665. The 190 proof ethanol is further dehydrated 670 to create a 200 proof ethanol 675 that is sold. During the dehydration process 670, any recovered water 680 is cycled back to the distillation process 660.

When the 190 proof ethanol is extracted during the distillation process 660, whole stillage 685 remains and is moved to a slurry tank 690 for the self generation of energy process 604. The whole stillage 690 is mechanically mixed with recycled water 692 and 694 and recycled bacteria 696 to create a mixed liquor 698. The mixed liquor 698, which is between 10% and 15% solids concentration is moved or pumped to the anaerobic digester 700.

The anaerobic digester 700 is a continuous flow biological reactor which is either plug flow or completely mixed. The mixed liquor is mixed in the digester either mechanically or by sparging with biogas. The anaerobic digester is heated to between 90° F. and 110° F. using heat from the combustion of biogas. The biogas 705 is collected from the headspace of the anaerobic digester 700 and used for: fuel in an internal combustion engine to produce electricity 710 and fuel for a boiler 715 to produce steam. The electricity produced is used to power mechanical systems in the ethanol production process 602 and the energy generation process 604. The steam produced in the boiler 715 is used in the production of ethanol. Waste heat is collected from the coolant of the internal combustion engine and the exhaust gas of the internal combustion engine using a fresh water system. The fresh water system is used to heat the anaerobic digester.

After being in the anaerobic digester 700 for 10 to 20 days, the mixed liquor 720 is pumped from the digester to solids separator 725, which may be a screw press. During the separation process digested solids or sludge 730 is separated from the digested liquid 735.

Bacteria 696 from the sludge 730 is recycled to the slurry tank 690, while the remaining sludge is sent to a dewatering process 740. During the dewatering process 740 any water is recycled 694 back to the slurry tank. The remaining solids are then sold as a sold amendment 745.

The digested liquid 735 is pumped into an ammonia stripper 750 for removal of the ammonia. The water 692 following ammonia removal is recycled back to the slurry tank 690. The off-gas 755 from the ammonia stripping tower goes into an ammonia recovery scrubber 760 where the ammonia is recovered at a high concentration in water. The concentrated ammonia solution 765 is then sold as fertilizer.

Figure 7:
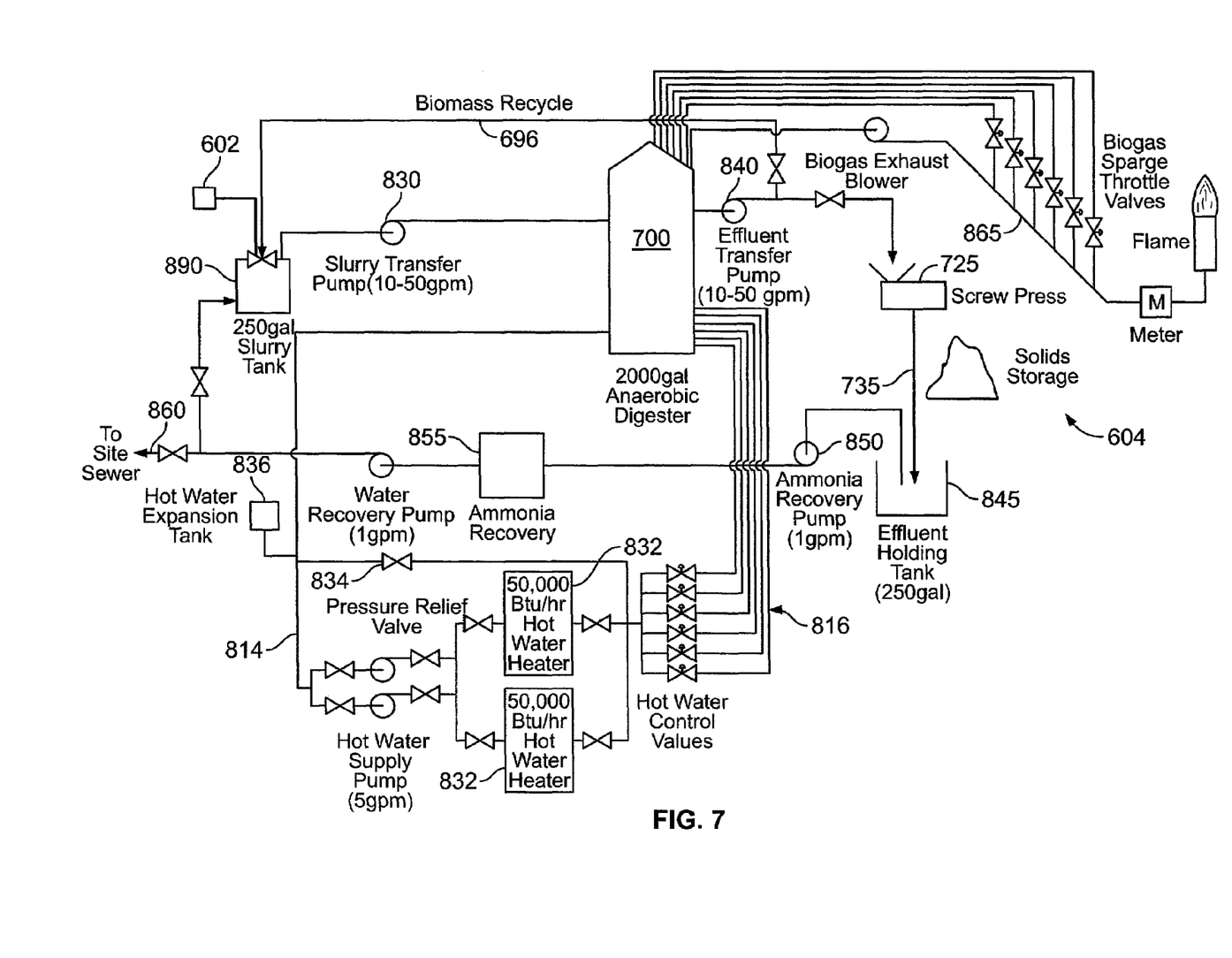
FIG. 7 is a schematic process flow diagram of a pilot scale anaerobic digester recovery system in accordance with an embodiment of the present invention.

In another embodiment of the present invention, shown in FIG. 7, it is desirable to provide an ethanol facility that is able to self-generate all of its own energy. This will be accomplished through the anaerobic microbial conversion of the whole stillage (ethanol production byproduct) to methane, ammonia, and stable (non-odorous) organic compost. The present invention will entail the alternative processing of whole stillage into energy ammonia fertilizer and an organic soil amendment and not into an animal feed. Laboratory results suggest that 11.6 million BTUs of methane can be produced per dry ton of whole stillage anaerobically digested. In addition, 85 lbs. of ammonia nitrogen is produced per dry ton of whole stillage digested. Using a natural gas price of $8/mmBTU, a DDGS price of $65/ton, an estimated capital cost for a digester to service a 50,000,000 gallon per year facility at $25 million, and an annual operating cost of $500,000, the internal rate of return (unleveraged) is greater than 20%.

The present invention has four objectives that address the questions necessary to validate the economic viability of the concept of producing all of the energy for ethanol production from anaerobic digestion of the whole stillage.

First, to determine the conversion of whole stillage to methane and carbon dioxide as a function of the hydraulic retention time. Technically DDGS can be anaerobcially converted to methane. The actual conversion must be determined because the economic viability relies on the heat value of the methane generated per ton of DDGS digested. The rate of conversion will dictate the size of the digester required and thus have a marked effect on the project capital cost.

Second, to determine biogas quality, treatment requirements for use of the biogas, and appropriate biogas treatment technologies to achieve the desired gas quality. Biogas is a mixture of methane and carbon dioxide. The ratio of methane to carbon dioxide will determine the heat content of the gas and thus its monetary value. Biogas can also contain ammonia and hydrogen sulfide. The combustion of ammonia and hydrogen sulfide can add to nitrogen and sulfur air emissions as well as causing the production of acids in the combustion chamber. Thus, evaluating biogas quality and the best available technology for the removal of ammonia and hydrogen sulfide will be critical for evaluating the economics of this concept.

Third, to determine the digested biomass consistency and appropriate technologies for dewatering. The anaerobically digested solids can be used in applications as top soil. The economic viability of the sale of these solids will depend on technology required to dewater them. Therefore, it will be important to determine the consistency of the digested solids (i.e., particle size distribution and water retention) in order to evaluate cost effective dewatering technologies.

Fourth, to determine appropriate technologies for ammonia recovery. Since DDGS is 29% protein, a significant amount of ammonia will be produced from the anaerobic digestion of the DDGS. The ammonia concentration must be managed in the anaerobic digester or it will inhibit the production of methane. The ammonia also has high market value as a fertilizer. Therefore, recovery of the ammonia is technically necessary and it will also provide additional revenue. The best available technology for ammonia recovery from digested liquid must be determined.

The first phase in implementation will include the design and construction of the energy generation system 604, illustrated in FIG. 7. The system 604 will consist of 2-1,000 gallon cylindrical anaerobic digester tanks 700 (also shown in FIGS. 8 and 9). Each tank 700 includes an interior support pipe 800 and a plurality of partitions 804 extending radially outwardly from the support pipe 800. The partitions 806 are held in place by support clips 806 positioned on the outer tank wall 807 and on the interior support pipe 800. Preferably, there are six partitions 804 that separate the each tank into six sectors 802 to create six complete mix digesters in series within each tank.

Figure 8:
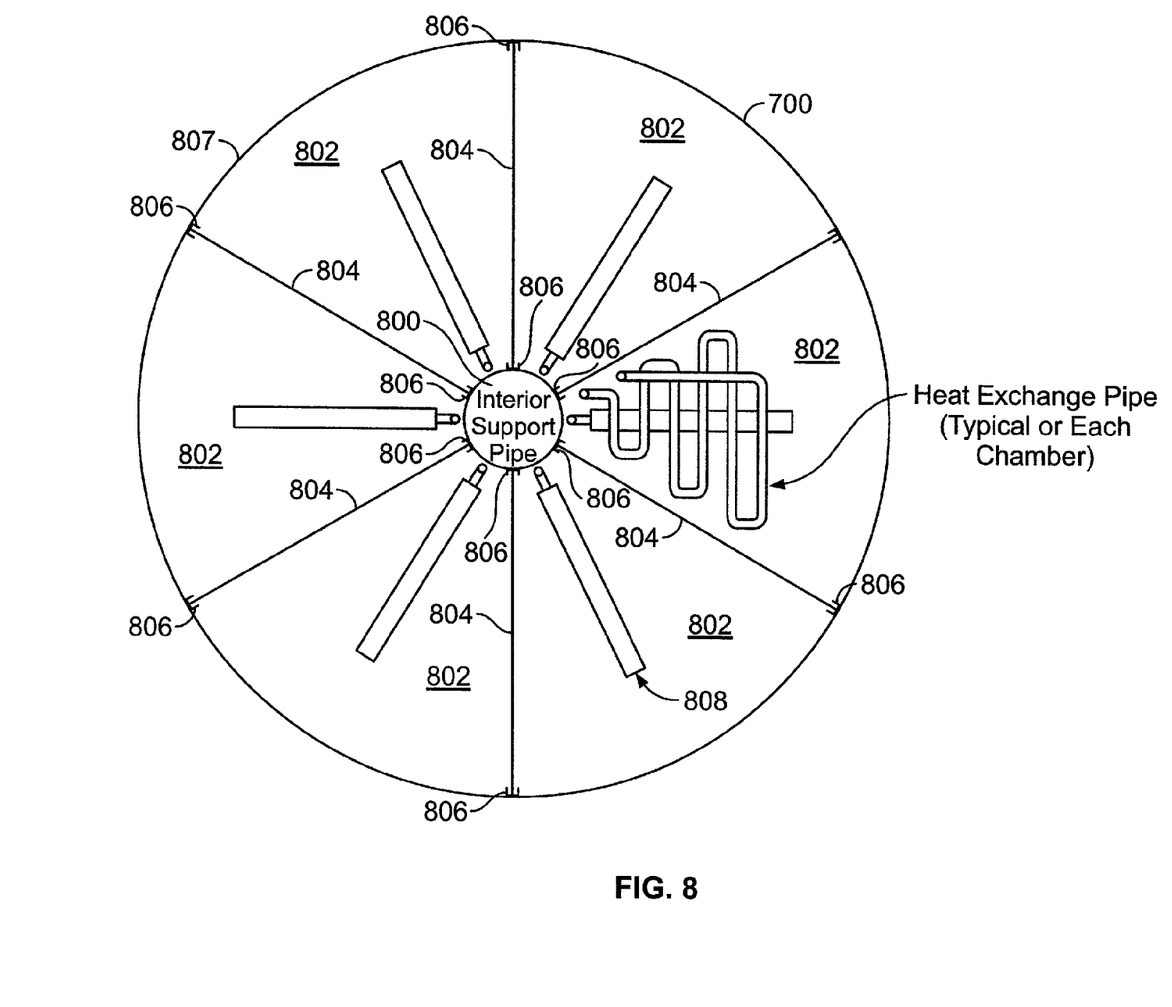
FIG. 8 is a top plan view of the anaerobic digester illustrated at FIG. 7.
Figure 9:
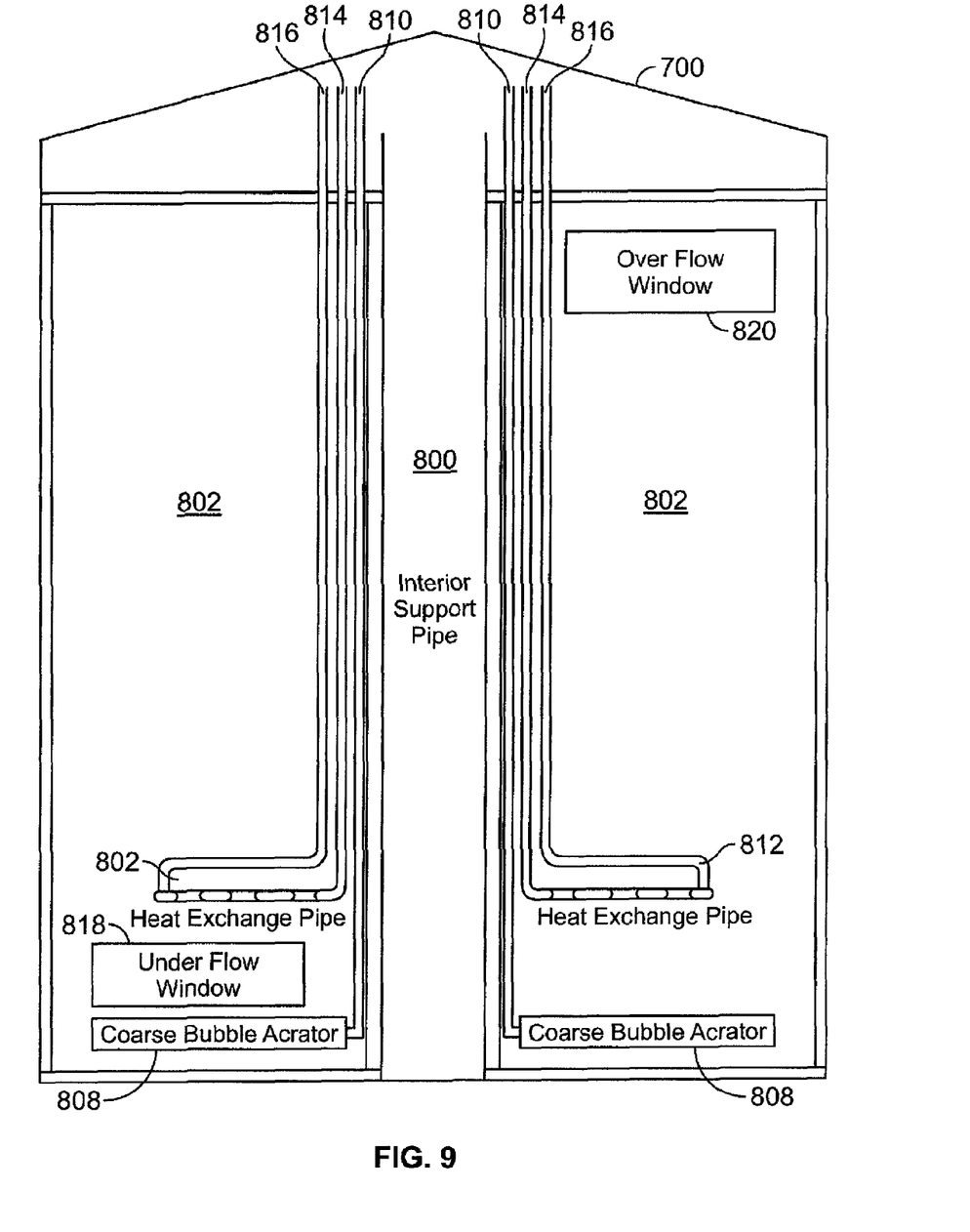
FIG. 9 is a sectional view of the anaerobic digester illustrated at FIG. 7.

To facilitate the biogas sparge mixing within the tank, each sector 802 includes coarse bubble aerators 808 near the bottom of the tank with biogas pipes 810 running upwardly along the interior support pipe 800. In addition, to heat and maintain the temperature of the mixed liquor in the tank heat exchange pipes 812 are provided with inflow pipes 814 and outflow pipes 816. Lastly, the tanks 700 may be provided with under flow 818 and over flow 820 windows.

Referring back to FIG. 7, the system 604 feeds the tanks 700 from the slurry tank 690. A slurry tank transfer pump 830 may be employed to help direct and control the amount off mixed liquor entering the tank. The whole sillage will enter the slurry tank 690 from the ethanol production process 602.

As mentioned the temperature of the tanks 700 is maintained and controlled by hot water. The water moves in and out of the tank by pipes 814 and 816. The water is first heated in water heaters 832. The heaters 832 will typically include a pressure relief valve 834 and a hot water expansion tank 836, because during heating of the water, the water will typically expand. Without the expansion tank 836, the pressure inside the inflow pipes 814 may become too strong and create shock waves or knocking. The water exiting the tank 816 is cycled back to the water heaters.

From the tank 700, the mixed liquor will be pumped 840 into the sold separator 724 or a screw press. The solids are stored and sold as soil amendment while the liquid 735 is moved into a holding tank 845 for the recovery of ammonia. A pump 850 is used to move the liquid 735 from the holding tank 845 to the ammonia recovery system 855. During the ammonia recovery, water is recovered or removed and possibly sent to a sewer 860.

The biogas is collected in the header or the tank and sent to the generators. Throttle valves 865 are used to control the flow of the biogas from the tanks 700.

During initial startup of the system 604, the digester 700 will consist of seeding and acclimatization. The digester will be seeded with a mixture of anaerobic sludge, raw manure, and whole stillage. Potable water will be added to create the mixed liquor with a solids content of 15%. Both digesters 700 will be filled with this mixed liquor and brought up to 100° F. using the hot water system. Once biogas production begins, biogas sparging will be initiated for mixing. The quantity and quality of biogas will be monitored continuously. Daily feed to the digesters 700 will be periodically increased slowly reducing the hydraulic retention time. Acclimatization will be complete when the digesters can receive 50 gallons of feed per day and have operated in this mode for one solids retention time (i.e., 20 days).

Digester 700 testing will commence once both digesters are acclimatized. Digester 1 will operate at 20 day solids retention for the remainder of the pilot scale study. The effluent from Digester 1 will be used to evaluate digested solids dewatering technologies and ammonia recovery technologies. The system will be equipped with a screw press which has been very effective for solids separation in manure anaerobic digestion systems. Several other technologies may also be used to determine the ability to remove and dewater digested solids, which may include VSEP (vibratory assisted membrane filtration), centrifuge, or filter press. In parallel with the solids dewatering evaluation, ammonia recovery technologies will also be evaluated. The system will have the AmmEL-HC system (ENPAR Technologies, Inc.), modified for ammonia recovery, installed. Recovery of ammonia using nanofiltration or reverse osmosis may also be used.

Digester 2 will be used to determine the effects of hydraulic retention time (HRT) on conversion of whole stillage to methane. Once acclimatization is complete, the volume of feed batch fed daily to the digester will be increased to reduce the HRT in 1-day increments. Digester 2 will operate at each new HRT for one HRT or until the daily methane generation rate is stable, which ever takes longer. The one day decreases in HRT will continue until the digester is operating at a 10 days HRT. This evaluation is expected to take up to 8 months.

Anaerobic digestion of whole stillage for self-generation of energy for an ethanol facility has three major benefits: increased energy efficiency, reduced financial risk, and support of sustainable agriculture. As mentioned above, anaerobic digestion of whole stillage has the potential of producing as much as 11.6 mmBTU per dry ton of whole stillage. This is more than sufficient energy to produce the steam and 75% of the electricity used to produce that ton of stillage. The recovery of 85 lbs. of ammonia nitrogen per dry ton of whole stillage is approximately 60% of the nitrogen fertilizer necessary for grow the corn in that ton of whole stillage. It is predicted that the anaerobic conversion of whole stillage to energy will increase the net energy value of a gallon of ethanol from 5,880 BTUs (USDA value) to 56,860 BTUs. Thus, anaerobic digestion of whole stillage represents a significant increase in the overall energy efficiency of the dry milling ethanol process.

The current financial model for an ethanol plant is plagued by the price volatility of four commodities: corn, DDGS, natural gas, and ethanol. By using the whole stillage to produce 89% of the energy for an ethanol facility, two volatile commodities are removed from the financial model reducing the financial risk for the production facility. It should noted that eliminating natural gas from the production process will have a very significant effect on the financial performance of ethanol facilities because of the current increasing trend in natural gas prices.

Historically, nutrient recovery from manure or agra-industry wastes has lead to over application of phosphorus because the nitrogen to phosphorus ratio in these wastes is not appropriate for agriculture. The anaerobic digestion of whole stillage with ammonia recovery will allow for the use of nitrogen as a fertilizer without any phosphorus. The majority of the phosphorus contained in the whole stillage will be precipitated in the anaerobic digester. The phosphorus will be part of the dewatered solids and will not be associated with the ammonia. Thus, anaerobic digestion allows for nutrient waste recovery without the detrimental effects of over application of phosphorus.

From the foregoing and as mentioned above, it is observed that numerous variations and modifications may be effected without departing from the spirit and scope of the novel concept of the invention. It is to be understood that no limitation with respect to the embodiments illustrated herein is intended or should be inferred.

It is claimed:

1. An integrated continuous process for the production of ethanol and self generating energy on a commercial scale after an initial process start-up, said integrated continuous process comprising the steps of:
    (a) fermenting a corn mash in an aqueous medium to produce a beer;
    (b) distilling said beer to produce commercial scale quantities of ethanol and a whole stillage;
    (c) digesting a mixture containing said whole stillage anaerobically in a digester tank to produce commercial scale quantities of a biogas and a residue, wherein the digester tank includes a plurality of sectors to create a series of mixing digesters;
    (d) combusting said biogas to produce electricity and steam;
    (e) utilizing steam produced by said combustion during the steps of fermenting and distilling to produce said ethanol; and (f) utilizing electricity produced by said combustion during the step of fermenting the corn mash;

said commercial scale of biogas being defined to include up to 11.6 million BTUs of methane per dry ton of said whole stillage anaerobically digested with the steam and electricity produced by step (d) being sufficient to provide, after said initial start up of said integrated continuous process, about 75% of the electricity of step (f) and all the steam of step (e) used to produce said ethanol and said whole stillage of step (b).

2. The process of claim 1 further comprising:
dehydrating the distilled ethanol to produce an ethanol with a higher proof than said distilled ethanol, wherein during the dehydrating step water is recovered.

3. The process of claim 1 further comprising mixing the whole stillage with bacteria and water prior to digesting.

4. The process of claim 1 further comprising the steps:
separating the residue from the digestion step into digested liquids and digested sludge, and
recycling bacteria from said digested sludge into the whole stillage.

5. The process of claim 4 further comprising the step:
dewatering the digested sludge to produce a soil amendment and a water residue.

6. The process of claim 5 further comprising the step:
recycling said water residue from the dewatering of the digested sludge into the whole stillage.

7. The process of claim 4 further comprising the steps:
recovering of ammonia from the digested liquid.

8. The process of claim 7 further comprising the step of recycling water from the digested liquid following ammonia recovery into the whole stillage.

9. The process of claim 1, wherein the step of digesting includes digesting in a tank that includes a plurality of sectors in series, wherein each sector is portioned from each other.

10. The process of claim 1 further comprising the step of separating said residue into a digested liquid and a sludge.

11. The process of claim 10 further comprising dewatering said sludge to produce a top soil amendment and a recyclable water residue.

12. The process of claim 10 further comprising recovering of ammonia from said digested liquid to produce an ammonia fertilizer.

13. The process of claim 1, wherein the plurality of sectors includes six sectors in series.

14. The process of claim 10, wherein the plurality of sectors includes six sectors in series.

15. An integrated continuous process for the production of ethanol and self generating energy on a commercial scale after an initial process start-up, said integrated continuous process comprising the steps of:

(a) fermenting a mash in an aqueous medium to produce a beer;
(b) distilling said beer to produce commercial scale quantities of ethanol and a whole stillage;
(c) digesting a mixture containing said whole stillage anaerobically in a digester tank to produce commercial scale quantities of a biogas and a residue;
(d) combusting said biogas to produce electricity and steam;
(e) utilizing steam produced by said combustion during the steps of fermenting and distilling to produce said ethanol; and
(f) utilizing electricity produced by said combustion during the step of fermenting the mash;

said commercial scale of biogas being defined to include up to 11.6 million BTUs of methane per dry ton of said whole stillage anaerobically digested with the steam and electricity produced by step (d) being sufficient to provide, after said initial start up of said process, about 75% of the electricity of step (f) and all the steam of step (e) used to produce said ethanol and said whole stillage of step (b).

* * * * *